United States Patent [19]

Lies et al.

[11] 4,044,127

[45] Aug. 23, 1977

[54] PROCESS FOR UTILIZING TETRAHYDRO-3-(4-PYRIDYLMETHYL)-2H-1,3,5-THIADIAZINE-2-THIONES AS FUNGICIDAL AGENTS

[75] Inventors: Thomas Andrew Lies, Montgomery Township, Somerset County; Herman Berenson, Trenton, both of N.J.

[73] Assignee: American Cyanamide Company, Stamford, Conn.

[21] Appl. No.: 725,754

[22] Filed: Sept. 23, 1976

Related U.S. Application Data

[62] Division of Ser. No. 665,656, March 10, 1976.

[51] Int. Cl.$^2$ ............................................. A01N 9/12
[52] U.S. Cl. .................................................. 424/246
[58] Field of Search ........................................ 424/246

[56] References Cited

U.S. PATENT DOCUMENTS

| 3,398,146 | 8/1968 | Schorr et al. | 260/243 |
| 3,475,422 | 10/1969 | Traber | 260/243 |
| 3,497,506 | 2/1970 | Traber | 260/243 |

*Primary Examiner*—Allen J. Robinson
*Attorney, Agent, or Firm*—Harry H. Kline

[57] ABSTRACT

There are provided tetrahydro-3-(4-pyridylmethyl)-2H-1,3,5-thiadiazine-2-thiones, a method for preparing the same, and a process for utilizing tetrahydro-3-(4-pyridylmethyl)-2H-1,3,5-thiadiazine-2-thiones in the control of plant pathogenic fungi.

10 Claims, No Drawings

PROCESS FOR UTILIZING TETRAHYDRO-3-(4-PYRIDYLMETHYL)-2H-1,3,5-THIADIAZINE-2-THIONES AS FUNGICIDAL AGENTS

This application is a divisional of our co-pending application, Ser. No. 665,656, filed on Mar. 10, 1976.

BACKGROUND OF THE INVENTION

Rieche et al. (Arch. Pharmaz. 293, 957 (1960) and 296,770 (1963) disclose the antifungal properties of 3-(phenylalkyl)tetrahydro-2H-1,3,5-thiadiazine-2-thiones. In (Arzneimittel Forschung, 19, 1807 (1969), Schorr et al. report that they prepared certain derivatives of tetrahydro-2H-1,3,5-thiadiazine-2-thione and conducted various chemotherapeutic studies with many of these compounds. These studies indicate that tetrahydro-2H-1,3,5-thiadiazine-2-thiones possess antifungal and antibacterial activity. Interestingly, Schorr et al. also found that derivatives of tetrahydro-2H-1,3,5-thiadiazine-2-thiones containing heteroaromatic substituents are markedly less active than the corresponding compounds in which the heteroaromatic ring has been replaced by an aromatic ring. For instance, replacement of a pyridylmethyl group with benzyl in said derivatives will significantly increase the biological activity.

It has been unexpectedly found that certain 5-substituted-tetrahydro-3(4-pyridylmethyl)-2H-1,3,5-thiadiazine2-thiones are highly effective fungicides characterized by markedly low phytotoxicity.

The 3-(4-(pyridylmethyl)-tetrahydro-2H-1,3,5-thiadiazine-2-thione compounds of the present invention are represented by formula (I):

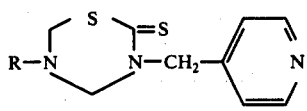

(I)

wherein R is a member selected from the group consisting of alkyl $C_1-C_{12}$, hydroxyethyl, —$CH_2COOH$, —$CH_2COONa$, —$CH_2CONH_2$ and the radical

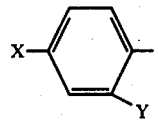

wherein X is selected from the group consisting of hydrogen, hydroxy and chloro, Y is hydrogen or methyl. The compounds are useful for the control of pathogenic fungi of agricultural crops being especially effective for the control of rice blast, tomato late blight, and apple scab.

Preferred compounds for the control of pathogenic fungi of agricultural crops are those of the above formula (I) wherein R is a member selected from the group consisting of methyl, ethyl, isopropyl, n-butyl, t-butyl, n-dodecyl, β-hydroxyethyl,

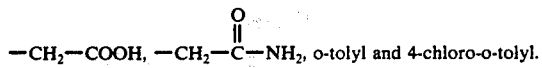

—$CH_2$—COOH, —$CH_2$—$\overset{O}{\overset{\|}{C}}$—$NH_2$, o-tolyl and 4-chloro-o-tolyl.

Illustrative of a method for preparing the compounds of the present invention involves reacting approximately equimolar amounts of 4-(aminomethyl)pyridine and and carbon disulfide in aqueous acetonitrile in the presence of a one molar equivalent of an alkali metal hydroxide, such as sodium hydroxide or potassium hydroxide, at a temperature from about 15° to about 30° C for a period from about 1 to 3 hours. There is then obtained the corresponding pyridylmethyldithiocarbamate of formula (II) as graphically illustrated hereinbelow:

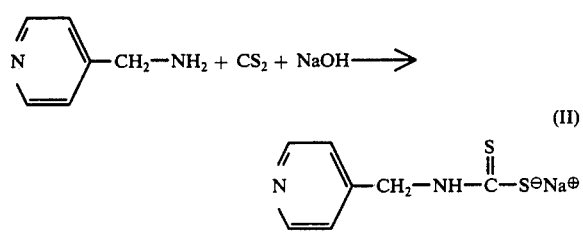

Next, the so-obtained dithiocarbamate is reacted with an aqueous solution of two molar equivalents of formaldehyde and an aqueous solution of a one molar equivalent of the appropriate R-$NH_2$ amine acid salt to yield the desired formula (I) tetrahydro-2H-1,3,5-thiadiazine-2-thione as graphically illustrated below:

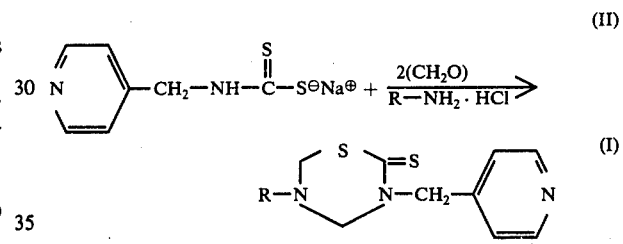

wherein R is as defined hereinabove.

In general, the fungicidal method of control of the present invention involves applying a fungicidally effective amount of a formula (I) compound to the foliage of agricultural crops where control of phytopathogenic fungi is desired. Application of a formula (I) tetrahydro-2H-1,3,5-thiadiazine-2-thione compound at a rate of from about 0.04 kg to about 8.96 kg per hectare and, preferably, from about 0.09 kg to about 4.48 kg per hectare is usually sufficient to achieve satisfactory control of said fungi without significant phytotoxic damage to the host crops.

Advantageously, the novel tetrahydro-2H-1,3,5-thiadiazine-2-thione compounds of the present invention represented by formula (I) above may be formulated as liquid or emulsifiable concentrates, wettable powders, dusts, dust concentrates and the like by well-known and commercially accepted methods.

Liquid and/or emulsifiable concentrates may be conveniently prepared by dissolving the appropriate formula (I) compound in amounts of about from 5 to 95% by weight and, preferably, 15 to 75%, by weight, in a solvent selected from the group consisting of water: $C_1-C_4$ aliphatic alcohols; ketones such as acetone, methyl ethyl ketone, methyl butyl isobutyl ketone, or cyclohexanone and the like; aromatic hydrocarbons such as benzene, toluene and xylene, aromatic petroleum distillates, or mixtures thereof. Additionally, 1% to 5% by weight of a surfactant, e.g. a polyoxyethylene sorbitan monolaurate surfactant or the like is incorporated into the above formulation. Application of the material is made by adding a predetermined quantity of the above concentrate as such or in combination with an additional quantity of water or another suitable inert solvent, e.g. deodorized kerosene.

Wettable powders can be prepared by milling and blending together between about 25% to 85% by weight of a compound of formula (I), a solid carrier such as attapulgite, kaolin, diatomaceous earth, silica and the like and about 1% to 5% by weight of a dispersing or wetting agent or mixtures thereof, such as sodium lignin sulfonate, N-methyl- N-oleoyltaurate and the like. In the above formulations the amount of solid carrier used is variable and obviously its value given in percent, by weight, is dependent on the amount of active ingredient and dispersing or wetting agent chosen for that particular formulation.

Dusts are generally prepared by blending and milling together from about 0.5% to 20%, by weight, of a tetrahydro-2H-1,3,5-thiadiazine-2-thione of formula (I) with an inert diluent such as an attapulgite type of clay, kaolin, diatomaceous earth, talc, fuller's earth and the like. Preferably, the dust contains from about 5 to 10%, by weight, of active ingredient and about 95 to 90%, by weight, of said inert diluent.

Dust concentrates are prepared similarly except that they contain usually from about 25 to 75% by weight of active ingredient and from 75 to 25% by weight of diluent.

The above formulations containing the appropriate formula (I) compounds of the present invention may be applied to the foliage of the agricultural crops to be protected by commercially available spraying and dusting equipment. For spraying, liquid or emulsifiable concentrates and wettable powders are diluted with water or another suitable inert solvent, such as deodorized kerosene, and applied as spray preparations of 100 ppm to 4800 ppm; or 0.090 kg to 4.48 kg per hectare.

The invention is further illustrated by the non-limiting examples set forth below.

EXAMPLE 1

Preparation of 5-Butyltetrahydro-3-(4-pyridylmethyl)-2H-1,3,5-thiadiazine-2-thione Carbon disulfide (7.6 g; 0.10 mole) is added to a cooled (15° C) and stirred solution of sodium hydroxide (4.0 g; 0.10 mole) and of 4-(aminomethyl)pyridine (10.8 g; 0.10 mole) in water (40 ml) and acetonitrile (50 ml). The temperature of the resulting mixture rises to 20° C. The cooling bath is removed and the mixture stirred at 20° C to 28° C for 50 minutes. The resulting mixture is then cooled to 19° C and an aqueous solution of formaldehyde (15.0 ml of 37% aqueous solution; 0.20 mole) is added. To this solution a solution of butylamine hydrochloride (prepared from 7.3 g, 0.10 mole of butylamine; 8.3 ml, 0.10 mole of conc. hydrochloric acid and 42 ml of water) is added. The resulting two-phase liquid mixture is stirred at ambient temperature for about 1 hour and is then cooled to 8° C and seeded (seeding solid obtained by cooling a drop of the reaction mixture to dry ice temperature). The resulting precipitate is filtered off, washed with water and air-dried. Recrystallization from 2-propanol yields 16.4 g of product, m.p. 75° C to 80° C. A second recrystallization from 2-propanol yields the pure product, m.p. 74.5° C to 81° C.

Analysis calculated for $C_{13}H_{19}N_3S_2$: C, 55.48; H, 6.80; N, 14.93. Found: C, 55.56; H, 6.69; N, 15.01.

TABLE I

Examples 2 to 14
By Employing the Procedure of Example 1, there are prepared the following in Table I below:

| Example | R | Melting Point (° C) |
|---|---|---|
| 2 | n-$C_{12}H_{25}$— | Sintering, then 72–75 |
| 3 | $CH_3$— | Sintering, then 171–175 |
| 4 | $C_6H_5$— | 187.5–189 Gas evolution |
| 5 | $HOCH_2CH_2$— | 139–145 Gas evolution |
| 6 |  | 196–199 Gas evolution |
| 7 | $(CH_3)_3C$— | 167–172.5 Gas evolution |
| 8 |  | Sintering, then 195–197 |
| 9 |  | 168–170 |
| 10 | $NaOOC-CH_2$— (hemihydrate) | 191–194-decomposition |
| 11 | $(CH_3)_2CH$— | 128–130 decomposition |
| 12 | $HOOC-CH_2$— | 169–173.5 Gas evolution |
| 13 |  | 156–158 |
| 14 | $H_2N-CO-CH_2$— | 170–172 decomposition |

EXAMPLE 15

Preparation of 5-(4-Pyridylmethyl)-3-butyltetrahydro-2H-1,3,5-thiadiazine-2-thione By the procedure of Example 1 sodium butyldithiocarbamate is prepared and reacted with formaldehyde and 4-(aminomethyl)pyridine hydrochloride to yield 5-(4-pyridylmethyl)-3-butyltetrahydro-2H-1,3,5-thiadiazine-2-thione.

The product is recrystallized from a choloroform hexane solution to give a 23% yield of product, m.p. 108° C to 111° C.

Analysis calculated for $C_{13}H_{19}N_3S_2$: C, 55.48; H, 6.8; N, 14,93; S, 22.79. Found: C, 55.36; H, 6.83; N, 14.89; S, 23.0.

EXAMPLE 16

To determine the effectiveness of the tetrahydro-2H-1,3,5-thiadiazine-2-thiones of the present invention as fungicidal agents, the following tests are carried out. Pathogens, host plants, the method of testing and the rating system used are reported below along with the data obtained.

Pathogens

*Piricularia oryzae* Cavara, the rice blast pathogen.
*Venturia inaequalis* (Cke.) Wint. which causes apple scab.
*Phytophthora infestans* (Mont.) Dby, the late blight fungus of tomato and potato.

Plants

Rice (*Oryza sativa;* Cv. Nato)
Apple (*Malus sylvestris*) Seedling
Tomato (*Lycopersicon esculentum;* Cv. Bonny Best)

Plants are individually grown in 5.1 cm peat squares and assembled in 7.6 × 25.4 cm fibre containers the week prior to spraying. With the exception of rice, a single specimen of each species is used.

Spray solutions containing the appropriate tetrahydro-2H-1,3,5-thiadiazine-2-thione compound are prepared at a final concentration of 50, 100, 200 or 500 ppm in 50 ml of 50% aqueous acetone. In all cases, acetone is added first to solubilize the compound and solutions made to final volume with deionized water.

Containers are sprayed simultaneously on a turntable with 50 ml of test solution. Spray is provided by two fixed nozzles mounted to deliver vertical and horizontal solid cone patterns. Immediately thereafter, all plants are returned to the greenhouse to permit the deposit to dry.

Plants are inoculated with conidial suspensions of the respective pathogens using a DeVilbiss paint sprayer operated at 0.28–0.42 kg/cm² pressure and immediately transferred to a controlled temperature/humidity cabinet (70° F, RH~ 95%) and are held 3–4 days in the cabinet, and then transferred to the greenhouse to await disease expression.

Performance Rating

All plants are rated for disease severity on a scale of 1–7 (clean-kill) as described in Table II – IV below:

| Rating | Description |
| --- | --- |
| 1 | Nil |
| 2 | Trace disease |
| 3 | Slight disease |
| 4 | Moderate disease |
| 5 | Heavy disease |
| 6 | Severe disease |
| 7 | Kill |

Ratings reflect only levels where effective control is observed and are mean ratings for all tests carried out with any given compound.

Table II

Evaluation of derivatives of tetrahydro-2H-1,3,5-thiadiazine-2-thione as foliar fungicides for the control of rice blast (*Piricularia oryzae* Cavara) at the indicated spray rates.

R—N(CH₂—S—C(=S)—N—CH₂—pyridyl)

| | Test I | Test II | | |
| --- | --- | --- | --- | --- |
| | Average of two replicates Rate of application in ppm | Average of two replicates Rates of application in ppm | | |
| R | 500 | 500 | 100 | 50 |
| n-C₄H₉— | 2.5 | 1.5 | 2.5 | 3.0 |
| n-C₁₂H₂₅— | 3.0 | 1.5 | 2.5 | 3.0 |
| CH₃— | 3.0 | 2.0 | 2.5 | 3.5 |
| HOCH₂—CH₂— | 3.5 | 3.0 | 2.5 | 3.0 |
| Cl-phenyl-CH₃ | 1.0 | 2.0 | 3.5 | 3.5 |
| (2-methyl-phenyl)- | 2.5 | 3.0 | 3.5 | 5.0 |
| Infected, untreated controls | 5.1 | 5.0 | | |

Table III

Evaluation of derivatives of tetrahydro-2H-1,3,5-thiadiazine-2-thione as foliar fungicides for the control of Tomato Late blight (*Phytophthora infestans* (Mont.) Dby) at the indicated spray rates.

| | Test I | Test II | | |
| --- | --- | --- | --- | --- |
| | Average of two replicates Rate of application in ppm | Average of two replicates Rates of application in ppm | | |
| R | 500 | 200 | 100 | 50 |
| n-C₄H₉— | 2.5 | 3.5 | 3.5 | 4.0 |
| CH₃— | 1.5 | 2.5 | 3.5 | 4.5 |
| (CH₃)₃C— | 2.0 | 3.5 | 3.0 | 4.0 |
| HOOC—CH₂— | 2.5 | 3.0 | 3.5 | 3.5 |
| H₂N—C(O)—CH₂— | 2.5 | 1.5 | 2.5 | 3.5 |
| Infected untreated controls | 6.0 | 6.0 | | |

Table IV

Evaluation of derivatives of tetrahydro-2H-1,3,5-thiadiazine-2-thione as foliar fungicides for the control of apple scab (*Venturia inaequalis* (Cke.) Wint) at the indicated spray rates.

| | Test I | Test II | | |
| --- | --- | --- | --- | --- |
| | Average of two replicates Rate of application in ppm | Average of two replicates Rates of application in ppm | | |
| R | 500 | 200 | 100 | 50 |
| n-C₄H₉— | 2.5 | 1.0 | 1.0 | 2.5 |
| CH₃— | 1.5 | 2.5 | 3.0 | 2.5 |
| HOCH₂—CH₂— | 1.0 | 3.5 | 2.0 | 4.0 |
| (CH₃)₃C— | 1.0 | 4.0 | 5.0 | 4.5 |
| (CH₃)₂CH— | 2.5 | 3.0 | 4.0 | 5.5 |
| Infected, untreated controls | 5.1 | | 4.3 | |

EXAMPLE 17

Utilizing the fungicidal evaluation procedure of Example 16, the foliar fungicidal activity of 5-butyltetrahydro-3-(4-pyridylmethyl-2H-1,3,5-thiadiazine-2-thione (a compound of the invention) is compared to its isomer: 3-butyl-tetrahydro-5-(4-pyridylmethyl)-2H-1,3,5-thiadiazine-2-thione. The data obtained are given in Table V below.

Table V

Evaluation of the fungicidal activity of 5-Butyltetrahydro-3-(4-pyridylmethyl)-2H-1,3,5-thiadiazine-2-thione against its positional isomer 3-butyltetrahydro-5-(4-pyridylmethyl)-2H-1,3,5-thiadiazole-2-thione for the control of selected pathogenic fungi at the indicated spray rates. Ratings are average of two replicates each.

| Compound | Pathogen | Rice Blast | | | | Tomato Late Blight | | | | Apple Scab | | | |
|---|---|---|---|---|---|---|---|---|---|---|---|---|---|
| | | Rates of Application in ppm | | | | Rates of Application in ppm | | | | Rates of Application in ppm | | | |
| | | Test I | Test II | | | Test I | Test II | | | Test I | Test II | | |
| | | 500 | 200 | 100 | 50 | 500 | 200 | 100 | 50 | 500 | 200 | 100 | 50 |
| 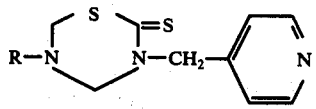 | | 2.5 | 1.5 | 2.2 | 3.0 | 2.5 | 3.5 | 3.5 | 4.0 | 2.5 | 1.0 | 1.0 | 2.5 |
| 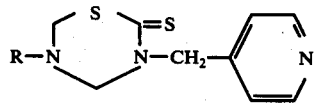 | | 2.0 | 4.5 | 5.5 | 5.5 | 2.0 | 5.5 | 6.0 | 6.0 | 4.0 | 4.5 | 4.0 | 4.5 |
| Untreated, infected controls | | 5.1 | — | 5.0 | — | 5.7 | — | 6.0 | — | 5.1 | — | 4.3 | — |

The above data clearly show that 3-butyltetrahydro-5-(4-pyridylmethyl)-2H-1,3,5-thiadiazine-2-thione is much less effective for the control of fungi, especially at lower rates of application, than is the novel compound of the invention: 5-butyltetrahydro-3-(4-pyridylmethyl)-2H-thiadiazine-2-thione applied at the same rates.

We claim:

1. A method for the protection of plants from fungi comprising applying to said plants a fungicidally effective amount of the compound of the formula:

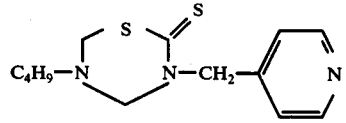

wherein R is selected from the group consisting of methyl, ethyl, isopropyl, n-butyl, tert-butyl, n-dodecyl, β-hydroxyethyl, carboxymethyl, carboxamidomethyl, o-tolyl and 4-chloro-o-tolyl.

2. The method according to claim 1, wherein R is methyl, n-butyl, n-dodecyl or β-hydroxyethyl.

3. The method according to claim 1, wherein said compound is 5-methyltetrahydro-3-(4-pyridylmethyl)-2H-1,3,5-thiadiazine-2-thione.

4. The method according to claim 1, wherein said compound is 5-n-butyltetrahydro-3-(4-pyridylmethyl)-2H-1,3,5-thiadiazine-2-thione.

5. The method according to claim 1, wherein said compound is 5-n-dodecyltetrahydro-3-(4-pyridylmethyl)-2H-1,3,5-thiadiazine-2-thione.

6. The method according to claim 1, wherein said compound is applied at a rate of from about 0.05 kg to about 8.96 kg per hectare.

7. The method according to claim 1, wherein said compound is applied at a rate of from 0.09 kg to about 4.48 kg per hectare.

8. The method according to claim 1, wherein said compound is applied at a rate of from 50 ppm to 4800 ppm.

9. The method according to claim 1, wherein said plants are rice, tomatoes and apples, and said fungi are rice blast, tomato late blight and apple scab.

10. A method for the control of phyte pathogenic fungi, comprising contacting said fungi with a fungicidally effective amount of the compound of the formula:

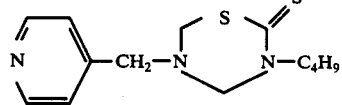

wherein R is selected from the group consisting of alkyl $C_1$-$C_{12}$, -$CH_2COOH$, -$CH_2COONa$,

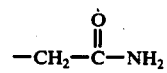

and the radical

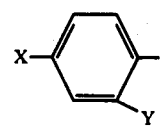

wherein X is hydrogen, hydroxy or chloro, and Y is hydrogen or methyl.

* * * * *